United States Patent [19]

Kameswaran

[11] Patent Number: 5,106,985
[45] Date of Patent: Apr. 21, 1992

[54] PROCESS FOR THE PREPARATION OF INSECTICIDAL, NEMATICIDAL AND ACARICIDAL 4-SUBSTITUTED-5-(TRIFLUOROMETHYL)-PYRROLE-3-CARBONITRILE COMPOUNDS

[75] Inventor: Venkataraman Kameswaran, Princeton Junction, N.J.

[73] Assignee: American Cyanamid Company, Stamford, Conn.

[21] Appl. No.: 614,541

[22] Filed: Nov. 16, 1990

[51] Int. Cl.$^5$ ............... C07D 401/04; C07D 207/30
[52] U.S. Cl. ............................... 546/281; 548/561; 548/562
[58] Field of Search ............... 546/281; 548/561, 562

[56] References Cited

PUBLICATIONS

Chemical Abstracts, vol. 111, No. 13, Abst. No. 111,037-X, Sep. 25, 1989.
Chemical Abstracts, vol. 111, No. 21, Abst. No. 194,576-W, Nov. 20, 1989.
Chemical Abstracts, vol. 113, No. 13, Abst. No. 115,076-Y, Sep. 24, 1990.

*Primary Examiner*—Alan L. Rotman
*Attorney, Agent, or Firm*—Peggy A. Climenson

[57] ABSTRACT

There is provided a process for the preparation of 4-substituted-5-(trifluoromethyl)pyrrole-3-carbonitrile compounds which are useful as insecticidal, nematicidal and acaricidal agents.

9 Claims, No Drawings

PROCESS FOR THE PREPARATION OF INSECTICIDAL, NEMATICIDAL AND ACARICIDAL 4-SUBSTITUTED-5-(TRIFLUOROMETHYL)PYRROLE-3-CARBONITRILE COMPOUNDS

BACKGROUND OF THE INVENTION

Arylpyrrole compounds useful as insecticides, nematicides and acaricides and their preparation are described in copending patent application Ser. No. 07/208,841, filed on Jun. 23, 1988, now U.S. Pat. No. 5,010,098. Also, diaryl-pyrrolecarbonitrile compounds useful as insecticides and acaricides and their preparation are also described in U.S. Pat. No. 5,010,098.

The processes of the copending applications are useful for the preparation of the above arylpyrrole and diarylpyrrole compounds. However, not all of the processes of the above copending patent applications are suitable for use in large scale preparations of the compounds. Therefore, it is desirable to find new methods for the preparation of arylpyrrole and diarylpyrrole compounds.

It is an object of the present invention to provide a novel and efficient process for the preparation of insecticidal, nematicidal and acaricidal 4-substituted-5-(trifluoromethyl)pyrrole-3-carbonitrile compounds.

SUMMARY OF THE INVENTION

The present invention relates to a process for the preparation of insecticidal, nematicidal and acaricidal 4-substituted-5-(trifluoromethyl)pyrrole-3-carbonitrile compounds of formula I

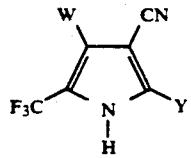

(I)

wherein
Y is hydrogen or W; and
W is phenyl optionally substituted with $CF_3$, $C_1$-$C_4$ alkyl, $C_1$-$C_4$ alkoxy, CN, $NO_2$, or one to three halogen atoms; α- or β-naphthyl; or 2-,3- or 4-pyridyl optionally substituted with $CF_3$ or one to three halogen atoms.

Said compounds and their use as insecticidal, nematicidal and acaricidal agents are described in co-pending patent application Ser. Nos. 07/208,841, filed on Jun. 23, 1988, now U.S. Pat. No. 5,010,098, which are incorporated herein by reference.

Surprisingly, it has been found that insecticidal, nematicidal and acaricidal compounds of formula I may be prepared by a novel and efficient process by way of a single step reaction between an oxime compound of formula II

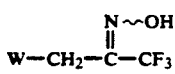

(II)

wherein W is as described above and a β-halo-α,β-unsaturated nitrile compound of formula III

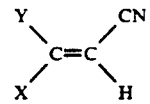

(III)

wherein Y is as described above; X is Cl, Br or I and the cis- nd trans- isomers thereof in the presence of a base and solvent.

DETAILED DESCRIPTION OF THE INVENTION

The present invention provides a process for the preparation of insecticidal, nematicidal and acaricidal compounds of formula I

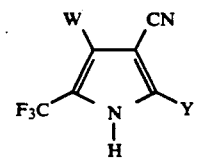

(I)

wherein
Y is hydrogen or W; and
W is phenyl optionally substituted with $CF_3$, $C_1$-$C_4$ alkyl, $C_1$-$C_4$ alkoxy, CN, $NO_2$, or one to three halogen atoms; α- or β-napthyl; or 2-,3- or 4-pyridyl optionally substituted with $CF_3$ or one to three halogen atoms;
by a single step reaction between an oxime compound of formula II

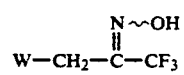

(II)

wherein W is as described above and a β-halo-α,β-unsaturated nitrile compound of formula III

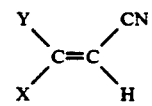

(III)

wherein Y is as described above; X is Cl, Br or I and the cis- and trans- isomers thereof in the presence of a base and solvent.

The process preferably comprises reacting a formula II oxime as described above with at least about one molar equivalent, preferably about one to four molar equivalents, of a formula III β-halo-α,β-unsaturated nitrile as described above and at least about one molar equivalent, preferably about one to four molar equivalents, of a base in the presence of a solvent preferably at a temperature range of about −5° C. to 35° C. to form 4-substituted-5-(trifluoromethyl)-pyrrole-3-carbonitrile compounds of formula I.

One of the preferred process of the present invention comprises reacting a formula II oxime wherein W is phenyl optionally substituted with $CF_3$, $C_1$-$C_4$ alkyl, $C_1$-$C_4$ alkoxy, CN, $NO_2$, or one to three halogen atoms with at least about one molar equivalent, preferably about one to three molar equivalents, of a formula III β-halo-α,β-unsaturated nitrile wherein Y is as described above; W is phenyl optionally substituted with $CF_3$, $C_1$-$C_4$ alkyl, $C_1$-$C_4$ alkoxy, CN, $NO_2$, or one to three halogen atoms; X is Cl or Br; and the cis- and trans-isomers thereof and at least about one molar equivalent, preferably about one to three molar equivalents, of a base in the presence of a solvent preferably at a temperature range of about 0° C. to 30° C. to form 4-substituted-5-(trifluoromethyl)pyrrole-3-carbonitrile compounds of formula I wherein Y is as described for formula I and W is phenyl optionally substituted with $CF_3$, $C_1$-$C_4$ alkyl, $C_1$-$C_4$ alkoxy, CN, $NO_2$, or one to three halogen atoms.

The product formula I compounds may be isolated by conventional techniques such as dilution of the reaction mixture with water and filtration of the formula I product or extraction of said product with a suitable solvent. In the isolation procedure any suitable extraction solvents may be employed, including water-immiscible solvents such as ether, ethyl acetate, toluene, methylene chloride and the like.

Bases suitable for use in the process of the invention include bases such as alkali metal $C_1$-$C_6$ alkoxides, alkali metal hydroxides, alkali metal carbonates, alkali metal hydrides, $C_1$-$C_4$ trialkyl-amines, sodium acetate and pyridine. Preferred bases are sodium methoxide, sodium hydride and potassium tert-butoxide.

Reaction solvents suitable for use in the above process include organic solvents such as ether, dioxane, tetrahydrofuran, toluene, xylene, chlorinated hydrocarbons and $C_1$-$C_6$ alcohols. Tetrahydrofuran and dioxane are preferred reaction solvents.

Certain starting formula II oximes may be prepared by reacting a formula IV compound having the structure

(IV)

wherein W is a described above for formula I with hydroxylamine hydrochloride in the presence of sodium acetate. The formula IV compounds are prepared according to the procedure of X. Creary, Journal of Organic Chemistry, 52, pages 5026-5030, 1987.

Certain starting formula III β-halo-α,β-unsaturated nitriles are prepared according to the procedures of F. Scotti, et al, Journal of Organic Chemistry, 29, pages 1800-1808, 1964 and J. Liebscher, et al, Journal Fur Praktische Chemie, band 325, pages 915-918, 1983.

In order to facilitate a further understanding of the invention, the following examples are presented to illustrate more specific details thereof. The invention is not to be limited thereby except as defined in the claims.

EXAMPLE 1

Preparation of
3-(p-Chlorophenyl)-1,1,1-trifluoro-2-propanone

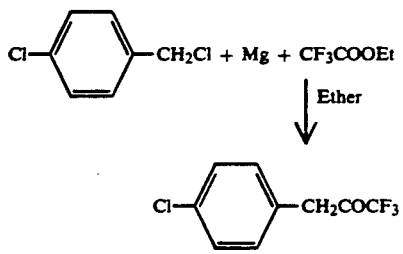

A solution of p-chlorobenzyl chloride (80.5 g, 0.5 mol) in anhydrous ether (150 mL) is slowly added to a vigorously stirred slurry of magnesium turnings (12.5 g, 0.5 mol) in ether (50 mL) over 45 minutes such that the reaction mixture maintains a moderate reflux. The solution is then refluxed for 30 minutes and cooled in an ice bath. The Grignard reagent is then added to a solution of ethyl tri-fluoroacetate (71.04 g, 0.5 mol) in ether (150 mL) at −60° to −70° C. (acetone-dry ice bath) over 45 minutes. The cooling bath is removed and the reaction mixture is allowed to warm to −10° C. whereupon a solid precipitates out. The reaction mixture is cautiously decomposed with saturated $NH_4Cl$ and then acidified with 10% HCl. The ether layer is separated, washed with water and saturated NaCl and dried ($MgSO_4$). Evaporation and vacuum distillation gives the title product as a clear liquid (52.8 g): bp 72°-74° C. (34 mm); IR (neat) 1762 $cm^{-1}$; $^1H$ NMR ($CDCl_3$) δ4.00 (s, 2H, $CH_2$), 7.15 and 7.35 (d, J=8.4 Hz, 4H, ArH); $^{19}F$ NMR δ-79.1; $^{13}C$ NMR; δ42.2 ($CH_2$) 116.7 (q $^1J_{CF}$=292.5 Hz, $CF_3$), 129.1 (C-2'); 131.0 (C-3'), 132.6 (C-1'), 134.0 (C-4'), 188.5 (q, $^2J_{CF}$=35.5 Hz, CO).

Following the procedure of example 1 but substituting benzyl chloride for p-chlorobenzyl chloride yields 1,1,1-trifluoro-3-phenyl-2-propanone as a clear liquid; bp 104-111° C. (house vacuum); IR (neat) 1762 $cm^{-1}$, $^1H$ NMR ($CDCl_3$) δ4.05 (s, 2H, $CH_2$) 7.2-7.5 (m, 5H, ArH); $^{19}F$ NMR δ-79.0 $^{13}C$ NMR δ43.0 (s, $CH_2$), 115.9 (q $^1J_{CF}$=292.7 Hz, $CF_3$), 189.0 (q, $^2J_{CF}$=35.1 Hz, CO).

EXAMPLE 2

Preparation of
3-(p-Chlorophenyl)-1,1,1,-trifluoro-2-propanone oxime,
(E)- or (Z)-

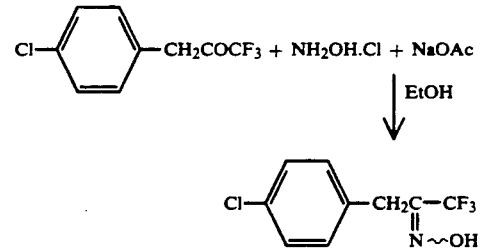

A solution of 3-(p-chlorophenyl)-1,1,1-trifluoro-2-propanone (10.0 g, 0.045 mol) in ethanol (60 mL) is treated with a solution of hydroxylamine hydrochloride (4.68 g, 0.067 mol) in water (20 mL) and then with a solution of sodium acetate (5.53 g, 0.067 mol) in water (20 mL). The reaction mixture is refluxed for 2 hours, cooled, diluted with water, and extracted with ether. The combined ether extracts are washed sequentially with water and brine, dried ($Na_2SO_4$) and evaporated to a liquid which solidifies upon standing to give the title compound as white needles (11.84 g): IR (neat) 3300 $cm^{-1}$ (broad); $^1H$ NMR ($CDCl_3$) δ3.86 (s, 2H, $CH_2$), 7.23 and 7.30 (AB,$J_{AB}$=8.6 Hz, ArH), $^{19}F$ NMR δ-69.2; $^{13}C$ NMR δ29.3 (s, $CH_2$), 120.8 (q, $^1J_{CF}$=274.5 Hz, $CF_3$), 128.8, 130.3, 132.5, 133.1 (Aromatic C), 148.4 (q $^2J_{CF}$=32.1 Hz, CO).

Following the procedure of example 2 but substituting 1,1,1-trifluoro-3-phenyl-2-propanone for 3-(p-chlorophenyl)-1,1,1-trifluoro-2-propanone yields 1,1,1-trifluoro-3-phenyl-2-propanone oxime, (E)- or (Z)- as a clear liquid; IR (neat 3300 $cm^{-1}$ (broad; $^1H$ NMR ($CDCl_3$) δ3.94 (s, 2H, $CH_2$), 7.3 (m, 5H, ArH), 9.8

(broad, OH); $^{19}$F NMR δ-69.1, $^{13}$C NMR δ30.0 (s, CH$_2$), 120.9 (q, $^1J_{CF}$=274.5 Hz, CF$_3$); 127.1 (C-1'), 128.7, 129.4 (C-2'and C-3'), 134.0 (C-4'), 149.0 (q, $^2J_{CF}$=32.1 Hz, CO).

EXAMPLE 3

Preparation of 4-(p-Chlorophenyl)-5(trifluoromethyl)-pyrrole-3-carbonitrile

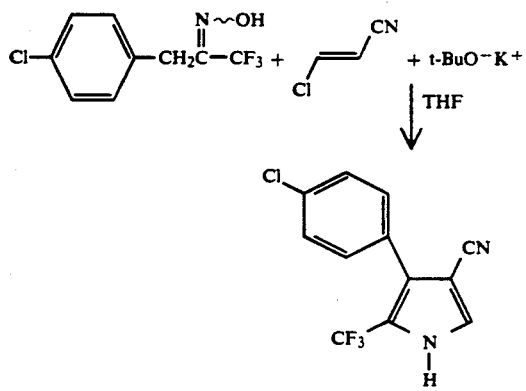

Potassium-t-butoxide (2.46 g, 0.022 mol) is added in portions to a solution of 3-(p-chlorophenyl)-1,1,1-trifluoro-2-propanone oxime, (E)-, or (Z)-(4.75 g, 0.02 mol) in tetrahydrofuran (20 mL) at such a rate that the temperature if maintained at 25°-30° C. (ice-water bath). The resulting solution is stirred for 15 minutes and then added dropwise to a solution of β-chloroacrylonitrile (1.75 g, 0.02 mol) in tetrahydrofuran (15 mL) at 15°-10° C. over ½ hour. The ice bath is removed and the reaction mixture is stirred for 1 hour, diluted with water, made acidic with a small amount of dilute HCl and extracted with ether. The combined ether extracts are washed with water and brine and dried (Na$_2$SO$_4$). Concentration in vacuo gives an oil which is dissolved in methylene chloride and filtered through a bed of flash column silica gel (30 mL size) and washed with an ethyl acetate/methylene chloride mixture (1:1). The filtrate is evaporated and the residual semi-solid is crystallized from methylene chloride/hexanes to give the title product as a yellow solid (2.10 g): mp 162.5°-164.0° C. IR (Nujol) 3200, 2250 cm$^{-1}$, $^1$H NMR (DMSO-d$_6$) δ7.42, 7.56 (AB, J$_{AB}$=8.3 Hz, ArH), 8.03 (s, 1H, 2H); $^{19}$F NMR δ-51.2; $^{13}$C NMR δ94.2 (C-3), 115.0 (CN), 116.6 (q, $^2J_{CF}$=38.3 Hz, C-5), 120.6 (q, $^1J_{CF}$=268.7 Hz, CF$_3$), 127.0 (q, $^3J_{CF}$=3.5 Hz, C-4), 128.6 (C-2') 129.1 (C-1'), 129.7 (C-2), 130.8 (C-3'), 133.4 (C-4').

Following the procedure of example 3 but substituting 1,1,1-trifluoro-3-phenyl-2-propanone oxime, (E)- or (Z)- (1.8 g) for 4-(p-chlorophenyl)-5-(trifluoromethyl)-pyrrole-3-carbonitrile as a white solid (1.4 g): mp 114.0°-115.0° C.; IR (Nujol) 3290, 3320, 2248 cm$^{-1}$; $^1$H NMR (DMSO-d$_6$) δ7.3-7.5 (m, 5H, ArH), 8.00 (d, J=1.6 Hz, 2H); $^{19}$F NMR δ-51.1; $^{13}$C NMR δ94.2 (C-3) 115.2 (CN), 116.4 (q, $^2J_{CF}$=38.3 Hz, C-5), 120.7 (q, $^1J_{CF}$=268.2 Hz, CF$_3$), 128.3, 128.5 129.0 (C-4', C-2', C-3'), 129.5 (C-2), 130.3 (C-1').

EXAMPLE 4

Preparation of 2,4-Bis(p-chlorophenyl)-5-(trifluoromethyl)pyrrole-3-carbonitrile A chilled (ice-water bath) solution of 3-(p-chlorophenyl)-1,1,1-trifluoro-2-propanone oxime (1.68 g, 0.007 mol) and tetrahydrofuran (10 mL) is treated portionwise with potassium t-butoxide (0.872 g, 0.0078 mol) over twenty minutes. After stirring for 15 minutes, this solution is added dropwise at 8° C. to a solution of β-chlorocinnamonitrile (1.48 g, 0.0071 mol) in 5 mL of tetrahydrofuran. The reaction mixture is stirred for 45 minutes, diluted with water, acidified with aqueous hydrochloric acid and extracted with ether. The combined organic extracts are washed sequentially with water and brine and concentrated in vacuo to give a gum. Trituration of the gum with an ether/hexanes mixture yields a solid. This solid is filtered off and the filtrate precipitates a brownish yellow solid which is recrystallized from ethyl acetate/hexanes to give the title product as a yellow solid (mp>250° C.), identified by IR and NMR spectral analyses.

I claim

1. A process for the preparation of a 4-substituted-5-(trifluoromethyl)pyrrole-3-carbonitrile compound having the structural formula

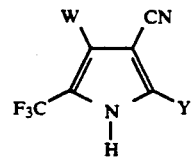

wherein

Y is hydrogen or W; and

W is phenyl optionally substituted with CF$_c$, C$_{d1}$-C$_4$ alkyl, C$_1$-C$_4$ alkoxy, CN, NO$_2$, or one to three halogen atoms; α- or β-napthyl; or 2-,3- or 4-pyridyl optionally substituted with CF$_3$ or one to three halogen atoms which comprises reacting an oxime compound having the structural formula II

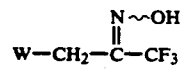

wherein W is as described above with at least about one molar equivalent of a β-halo-α,β-unsaturated nitrile compound having the structural formula III

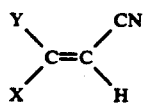

wherein Y is as described above, X is Cl, Br or I and the cis- and trans- isomers thereof in the presence of at least about one molar equivalent of a base and a solvent to form the 4-substituted-5-(trifluoromethyl)-pyrrole-3-carbonitrile compound.

2. The process according to claim 1 wherein the β-halo-α,β-unsaturated nitrile is present in the amount of about 1 to 4 molar equivalents.

3. The process according to claim 2 wherein the base is present in the amount of about 1 to 4 molar equivalents.

4. The process according to claim 1 wherein the base is selected from the group consisting of an alkali metal $C_1$–$C_6$ alkoxide, an alkali metal hydride and an alkali metal hydroxide.

5. The process according to claim 4 wherein the solvent is selected from the group consisting of an ether, dioxane, toluene, tetrahydrofuran and a $C_1$–$C_6$ alcohol.

6. The process according to claim 1 wherein the temperature of the reaction mixture is about $-5°$ C. to $35°$ C.

7. The process according to claim 1 wherein W is phenyl optionally substituted with a substituent selected from the group consisting of $CF_3$, a $C_1$–$C_4$ alkyl, a $C_1$–$C_4$ alkoxy, CN, $NO_2$, and one to three halogen atoms.

8. The process according to claim 7 wherein X is Cl.

9. The process according to claim 7 wherein X is Br.

* * * * *